United States Patent [19]

Dragan

[11] Patent Number: 4,704,087

[45] Date of Patent: Nov. 3, 1987

[54] RETAINERLESS MATRIX BAND

[76] Inventor: William B. Dragan, 85 Burr St., Easton, Conn. 06612

[21] Appl. No.: 848,799

[22] Filed: Apr. 7, 1986

[51] Int. Cl.⁴ .............................................. A61C 9/00
[52] U.S. Cl. ........................................ 433/39; 433/40
[58] Field of Search ............................ 433/39, 40, 126

[56] References Cited

U.S. PATENT DOCUMENTS

| 2,891,313 | 6/1959 | Crowley | 433/39 |
| 4,373,915 | 2/1983 | Comstock | 433/126 |
| 4,449,928 | 5/1984 | Weissenfluh | 433/40 |

FOREIGN PATENT DOCUMENTS 3014278  11/1980  Fed. Rep. of Germany ........ 433/39

*Primary Examiner*—Robert Peshock
*Attorney, Agent, or Firm*—Arthur T. Fattibene

[57] ABSTRACT

A retainerless dental matrix band which is preformed or contoured and which can be readily retained in place without a retaining tool. The matrix band comprises a curvilinear base portion having a connected upwardly and outwardly curved portion adapted to complement the shape of a tool and arranged to be disposed within the interproximal space between adjacent teeth, and fixedly retained in place by wedges and/or by bonded cotton pellets. The matrix is constructed for use with self cured or light cured composite resin dental material, and may be made of a light permeable material when used with light-cured composite materials.

6 Claims, 6 Drawing Figures

RETAINERLESS MATRIX BAND

FIELD OF INVENTION

This invention relates to matrix bands for teeth, and more specifically to a retainerless matrix band.

PROBLEM AND PRIOR ART

In the art of dentistry, matrix bands are frequently used in a tooth restoration procedure, e.g. in a class II restoration and in other dental procedures. Essentially, the matrix band is used to define the support, form and separation for optimum tooth restoration. The primary function of a matrix is to restore the anatomical contour and contact areas of a restored tooth.

Heretofore, the known matrix bands took on various forms and required the use of a retainer tool or other type of tool for placing and/or maintaining the matrix in place during a tooth restoration procedure, as disclosed in a Meer Dental Catalogue which is known to have been published. The most commonly known matrix comprised an elongated band or strip of flat material which required the folding of the strip to form a loop and the use of a retainer to tighten the loop around the tooth being restored. Such bands were generally formed of flat thin strips of a metal or plastic material free of any contour. Accordingly, such strip had to be contoured by the dentist as by burnishing.

Other so-called retainerless matrix bands required the use of a tightening device to fit a ring shaped band to a tooth. One such ring shaped band is currently sold under the trademark "Auto Matrix" and it requires the use of extraneous tools such as an "Automate III" tightener device and an "Auto Matrix" snipper tool to place the band on a tooth. Such ring shaped bands being devoid of any contour, also required contouring by burnishing it with an egg-shaped burnisher. Also, such ring shaped matrix band was relatively complex in structure and required a relatively tedius and time-consuming procedure to properly place the band about a tooth.

Also, due to the nature of the newer composite resins, which are taking the place of amalgam as a filling material, the known matrix bands have much to be desired when used with such composite resin materials. This is because the composite resin materials, being a semi-solid or semi-fluid, cannot be condensed as with amalgam. Because composite materials cannot be compressed, the non-contoured matrix strips are not suitable for achieving the desired contact and/or contour of a restored tooth when used with non-compressable composite filling materials.

OBJECTS

An object of this invention is to provide an improved matrix band or form which is contoured and which is particularly suitable when used with composite resin materials.

Another object is to provide an improved contoured matrix band or form which can be used with self-cured or light-cured composite materials.

Another object is to provide a contoured matrix band or form which can be readily applied to a tooth without the use of a retainer tool or tightening device.

Another object is to provide a contoured matrix band or form which is relatively simple in construction, easy to fabricate and which is positive in operation.

Another object is to provide a contoured matrix band or form which can be used singly or in pairs, depending upon the nature of the restoration, i.e. whether a two surface or a three surface restoration is to be performed.

SUMMARY OF THE INVENTION

The foregoing objects and other features and advantages are attained by a contoured matrix band that is preformed of a suitable thin material, preferably a light permiable plastic material. The thickness of the material forming the band is sufficiently thin to be fitted between adjacent teeth, and sufficiently rigid to maintain its pre-formed contour. The matrix band is provided with a lower generally semi-cylindrical base portion adapted to circumscribe a portion of the tooth adjacent the gingival line or gum line and an upper connected portion which is preformed to the shape of the tooth structure. The matrix band is thus generally C-shape in configuration so that it can be readily fitted to the tooth to define the necessary form for retaining the composite filling material. The matrix is secured in place by one or two wedge shaped pins disposed normal thereto and/or by a small cotton pellet or bead of light cured bonding material disposed on the Buccal and Lingual portions of the matrix band.

FEATURES

A feature of this invention resides in the provision whereby the contoured or preformed matrix band can be readily applied to the tooth and maintained in position without the use of a retainer and/or other extraneous tools such as tightener and snipper.

Another feature resides in the provision whereby the contoured retainerless matrix band can be readily formed of a transparent or light permeable material which renders it particularly suitable for use with light curing composite resin materials.

Another feature resides in the provision of a contoured matrix band that is simple to understand and use.

Another feature resides in the provision of a contoured matrix band that makes possible a restoration with predictable contacts.

Another feature of this invention resides in the provision of a matrix band construction which is sufficiently rigid to maintain its pre-formed contour and which is sufficiently flexible to conform to the tooth structure to be restored.

Other features and advantages will become more readily apparent when considered in view of the drawings and specifications in which.

DETAILED DESCRIPTION

Figure 1:
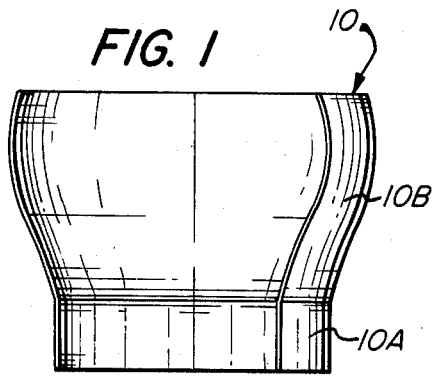
FIG. 1 is a side elevation view of a matrix band of the present invention.

Referring to the drawings, there is shown therein an improved matrix band or form construction 10 which are particularly suitable for use in Class II restorations of two or more surfaces. The matrix band construction as herein described is particularly suitable for use with self cured or light cured composite resin filling material which are gradually replacing amalgam materials heretofore used for Class II restorations. A Class II restoration has been classically defined as a posterior tooth having two or more surfaces that require restoration. However, there may be other dental procedures in which the matrix band construction as herein described may be used.

Amalgams heretofore used for such tooth restorations comprised a filling material that could be readily compressed. For this reason, in order to obtain a tight contact with the tooth, a dentist has to apply considerable force. To retain the amalgam material, it is essential that a matrix band, preferably formed of metal, be encircled about the tooth and retained firmly about the tooth by a retainer tool, e.g. a Toffelmeyer retainer. The matrix was required to contain the amalgam as it was compressed.

As composite resin materials are rapidly replacing amalgams as a preferred material for posterior restorations, the matrix bands and/or techniques heretofore used are not well suited for use with such composite resin materials. This is because composite resin filling materials cannot be compressed. Because composite resins cannot be compressed, being semi-fluid or semi-solid in its initial physical state, the composite resin requires a form to maintain the shape thereof.

Figure 2:
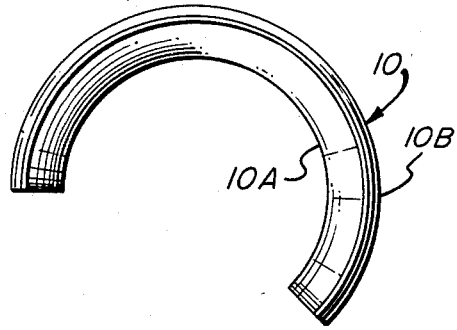
FIG. 2 is a top plan view of FIG. 1.
Figure 4:
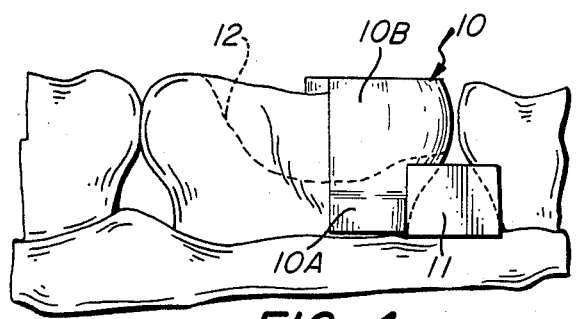
FIG. 4 is a side elevation view of FIG. 3.

In accordance with this invention, there is provided a matrix band construction 10 which is preformed to function as a "mold" for retaining and forming the composite resin filling material during a restoration procedure. As shown, the matrix band 10 is preferably preformed or contoured as shown in FIGS. 1 and 2. The matrix band 10 as illustrated comprises a lower collar or base portion 10A which is generally cylindrical in shape and which has a circumference defining a segment of a circle, e.g. more than 180° or less than 360°. The illustrated embodiment has the base or collar portion traversing approximately 225°. Extending upwardly from the base or collar portion 10A is a tooth engaging portion 10B that curves upwardly and outwardly as shown. The entire matrix has a thickness of approximately 0.0010–0.0030/inches, and a height of approximately 0.285 inches. The upper portion 10B is also formed to traverse a circumferential portion of a circle which is co-extensive to the base portion 10A. While the matrix band 10 may be formed of contoured thin sheet metal, the preferred material is to form the described matrix band construction of a plastic material which is sufficiently rigid to maintain the described preformed or contoured shape described, and which pre-formed shape is sufficiently flexible to conform to the shape of the actual tooth against which the matrix band 10 is applied. Because light cured composites are gaining popularity as a posterior filling material, the matrix band 10 may be formed of clear, transparent or light permeable material. For self-cured composite resins, the "color" or light permeable nature of the material from which the band can be made is not critical.

Figure 3:
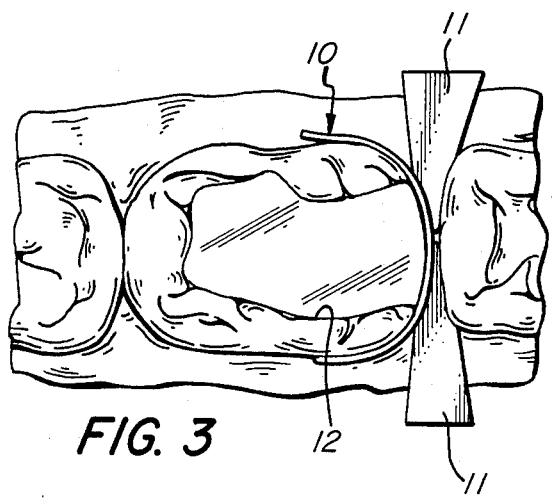
FIG. 3 is a top plan view of a matrix band of the invention as applied to a two-surface restoration of a Class II type.

To retain the described matrix band 10 in position relative to the tooth to be restored, contour band 10 is interposed interproximal between the tooth to be restored and the next adjacent tooth as shown in FIG. 3. The base or collar portion 10A is then tightly secured by wedges or wedge shaped pins 11 against the gingival margin. Ideally, a wait of approximately two minutes or so is recommended after wedging the band 10 in place to allow time for a slight separation of the teeth to occur because of the wedging. In addition to the wedges or in lieu of the wedges, the matrix band can be secured in place by a small cotton pellet or sponge soaked in a bonding liquid that can be cured in place to help hold the Buccal and Lingial portion of the matrix band 10 in place.

With the matrix so positioned, as shown in FIG. 3, and positively held in place without a retainer tool, the cavity or restoration is readied for receiving the composite resin filling material. As the resin material is placed in the cavity 12, a portion of which is defined by the matrix band 10, e.g. by syringe injection, the cavity will fill from the bottom up with the resin material being contained by the pre-formed or contoured matrix band 10. Because composite resin filling material is initially a semi-fluid or semi-solid, it cannot be compressed like amalgam. Therefore, there is little chance of any extrusional material beyond the floor of the cavity tightly contained by the wedged matrix band 10.

The arrangement is such that the matrix band which is pre-contoured, defines or creates the exact contact area needed with the adjacent tooth, rather than upon the dependent of the condensation of an amalgam material to force the matrix band against the approximating tooth.

Once the material of the restoration has cured, either by light curing or self curing, the matrix band 10 can be readily removed by removal of the wedges 11.

Figure 5:
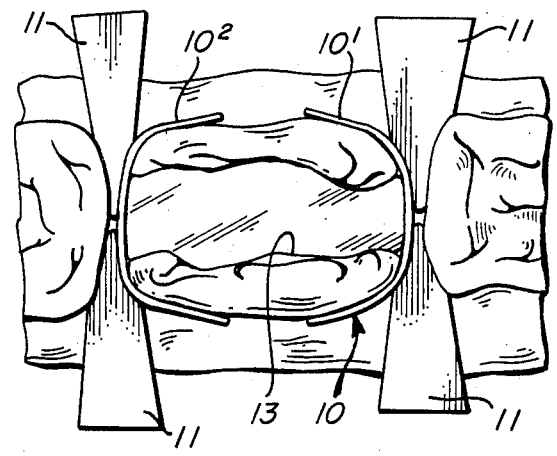
FIG. 5 is a top plan view of a matrix band of the invention as applied to a three surface tooth restoration of a Class II type.

For effecting a Class II restoration having more than two surfaces, as shown in FIG. 5, two matrix bands 10 as described are used. As shown, one matrix band $10^1$ is disposed on the mesial side and the other band $10^2$ is disposed on the distal side. Each band $10^1$ and $10^2$ are wedged in place as herebefore described. With the bands $10^1$ and $10^2$ thus retained in place, without retainers, the cavity 13 is filled as hereinbefore described.

From the foregoing description, it will be apparent that the preformed or contoured band 10 provide a relatively simple matrix band which positively defines a form for non-compressible filling material that insures the appropriate contact point with the next adjacent tooth, and which will prohibit any excess filling material from being forced beneath the cavity preparation and into the gingival sulcus. As described, the matrix band can be simply placed between the teeth and secured in place totally without a retainer tool.

Also, by forming the band 10 of a clear plastic or celluloid type material, a light cured filling material can be readily cured by projecting the curing light beam through the matrix. If desired, the wedges may also be made of light permeable material. With the described matrix band, a predictable contact point can be secured since such contact is not dependent upon the compressive forces imparted, as with amalgam, which distorted the prior known matrix bands even when retained in place by a retainer tool.

As the matrix band 10 determines the form of the composite resin restoration, the preforming or the contouring thereof is such that it creates or approximates a tight contact with the next adjacent tooth. By forming such tight contact with the next adjacent tooth, an open space to form a food trap is avoided. Not only do such open spaces define an uncomfortable foot trap; such food traps provide a potential source for developing a periodontal pocket resulting in further problems and possibly the eventual loss of the tooth.

The described matrix band, being devoid of a retaining tool for maintaining the band in place, renders an unobstructed working area for the dentist which is inherently limited.

Figure 6:
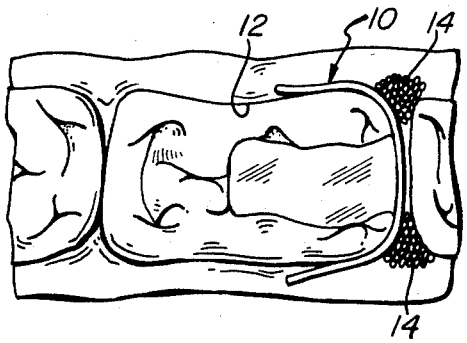
FIG. 6 is a plan view of a modified arrangement.

FIG. 6 illustrates a modified means for holding the matrix band 10 in place. In this form, the matrix band 10 is similar to that herein decribed. However, in this form of the invention, the band 10 is held in place by cottom pellets 14 which have been saturated with a bonding agent and cured in place. Thus, the cotton pellets 14—14 provide the means for holding the matrix band in place. In all other respects, the embodiment of FIG. 6 is similar to that hereinbefore described.

From the foregoing, it will be noted that the C shaped or contoured band 10 is sufficiently resillient so that it will conform and generally snap to hug or fit the shape of the tooth to provide for the proper placement and to define the contact area for the restoration with the adjacent tooth. Further, the contoured band 10 can be more quickly and more expediently fitted to the tooth because of its shape and resiliency than with the prior kown matrix bands that required a retainer tool and/or a tightener device. The preformed matrix band 10 being C shaped and pre-formed embraces the tooth so as to define only the surface to be restored, without the need of requiring a dentist to conform a matrix band about the entire 360° of a tooth as with the prior known matrix bands.

While the invention has been described with respect to a particular embodiment, variations and modifications may be made wtihout departing from the spirit or scope of the invention.

What is claimed is:

1. A matrix form for effecting a Class II restoration, i.e. posterior tooth having two or more surfaces that require restoration with a non-compressive composite resin filling material comprising
    a pre-formed contoured form made of relatively thin sheet plastic material sized to be fitted into the interproximal space between adjacent teeth,
    said form being generally C shaped in configuration and having a generally semi-cylindrical base portion and a connected tooth conforming portion contoured so as to approximate the contact surface of the tooth to be restored with the next adjacent tooth,
    said form being sufficiently rigid so as to retain its generally pre-formed C shaped configuration and sufficiently flexible so as to snap fit onto the tooth to be restored,
    a wedging means for retaining said matrix form in place adjacent to the tooth to be restored, and for effecting a slight temporary separation of the adjacent teeth,
    said wedging means being frictionally retained between said base portion of said form and the next adjacent tooth at the gingival margin whereby said form defines a passive matrix for conforming the non-compressible composite resin material to the shape of the tooth contact surface when cured.

2. A matrix form as defined in claim 1, wherein said form is made of a light permeable plastic material for use with light curable composite resin restorative dental materials.

3. A matrix form as defined in claim 2, wherein said form has a thickness in the range of approximately 0.0010 inch to 0.0030 inch.

4. A tooth restoration technique for effecting a Class II tooth restoration, i.e. a posterior tooth having two or more surfaces to be restored with a non-compressive composite resin filling material comprising the steps of:
    removing the defective enamel and carious dentin of a tooth for a Class II preparation for restoring the same with a non-compressible composite resin filling material,
    placing a matrix form that extends only about a portion of the tooth to be restored, whereby the said matrix form is disposed in the interproximal space between the tooth to be restored and the next adjacent tooth, said matrix form being disposed opposite the removed side surfaces of the tooth to be restored, whereby said matrix form simulates the contact surface for the tooth to be restored,
    securing the matrix form in position opposite the removed portion of the tooth to be restored by wedging said matrix form in place in said interproximal space whereby said wedging effects a slight temporary separation of said adjacent teeth while retaining said form opposite the removed portions of the tooth to be restored,
    placing a non-compressive composite resin in said prepared tooth whereby said non-compressive composite resin conforms to the shape of said matrix form to define the contact surface of the restored tooth,
    curing said composite resin in place with said matrix form retained in place, and
    removing said matrix form upon the curing of said composite resin whereby the restored tooth is provided with a predictable contact surface as defined by said matrix form.

5. A tooth restoration technique, as defined in claim 4, and including the steps:
    of placing a matrix form made of a light permeable plastic material in said interproximal space, using a light activated composite resin material for filing the prepared portion of said tooth to be restored,
    and curing said light activated material by exposing it to a curing light beam.

6. A matrix band for use in dentistry comprising a generally C shaped band formed of sheet material,
    said band being sufficient rigid so as to retain its generally C shaped configuration, and rendered sufficiently flexible so as to conform to the shape of a tooth to be restored,
    said band being sufficiently thin so as to be fitted between the interproximal space between a tooth to be restored and its adjacent tooth,
    said band defining the surface of the tooth to be restored,
    and wedge means for retaining said matrix band in place adjacent the tooth to be restored,
    said wedge means being frictionally retained between said band and the next adjacent tooth,
    and said wedge means effecting a slight temporary separation between the adjacent tooth and the tooth to be restored,
    wherein said wedge means comprises cotton pellets saturated with a bonding agent and temporarily cured in place to retain said band in place.

* * * * *